United States Patent
Petito et al.

(10) Patent No.: US 6,645,948 B2
(45) Date of Patent: *Nov. 11, 2003

(54) NUTRITIONAL COMPOSITION FOR THE TREATMENT OF CONNECTIVE TISSUE

(76) Inventors: George D. Petito, 1890 Bucknell Dr., Bethlehem, PA (US) 18015; Anita M. Petito, 1890 Bucknell Dr., Bethlehem, PA (US) 18015

( * ) Notice: Subject to any disclaimer, the term of this patent is extended or adjusted under 35 U.S.C. 154(b) by 0 days.

This patent is subject to a terminal disclaimer.

(21) Appl. No.: 10/287,590

(22) Filed: Nov. 5, 2002

(65) Prior Publication Data

US 2003/0069171 A1 Apr. 10, 2003

Related U.S. Application Data

(63) Continuation-in-part of application No. 09/360,169, filed on Jul. 26, 1999, now Pat. No. 6,476,005, which is a continuation-in-part of application No. 09/046,710, filed on Mar. 24, 1998, now abandoned.

(51) Int. Cl.$^7$ .................. A61K 31/7008; A61K 38/16; A61K 35/32
(52) U.S. Cl. .................. 514/62; 514/2; 514/54; 424/449
(58) Field of Search .................. 514/62, 2, 54; 424/449

(56) References Cited

U.S. PATENT DOCUMENTS

| | | |
|---|---|---|
| 1,950,100 A | 3/1934 | Crandall, Jr. |
| 4,006,224 A | 2/1977 | Prudden |
| 4,216,204 A | 8/1980 | Robertson |
| 4,455,302 A | 6/1984 | Robertson |
| 4,837,024 A | 6/1989 | Michaeli |
| 5,141,928 A | 8/1992 | Goldman |
| 5,252,339 A | 10/1993 | Cristofori et al. |
| 5,364,845 A | 11/1994 | Henderson |
| 5,442,053 A | 8/1995 | della Valle et al. |
| 5,498,606 A | 3/1996 | Soll et al. |
| 5,587,363 A | 12/1996 | Henderson |
| 5,840,715 A | 11/1998 | Florio |
| 5,929,050 A | 7/1999 | Petito |
| 6,476,005 B1 * | 11/2002 | Petito et al. .................. 514/62 |

FOREIGN PATENT DOCUMENTS

| | | |
|---|---|---|
| DE | 3445324 | 12/1986 |
| FR | 2035781 | 12/1970 |
| GB | 896940 | 5/1962 |

OTHER PUBLICATIONS

Body Ammo Nutraceuticals, "Product Alert", Oct. 27, 1997.
Richardson Labs, Inc., "Lookout (Non Foods Edition)", (Sep. 9, 1997).

* cited by examiner

*Primary Examiner*—James O. Wilson
*Assistant Examiner*—Devesh Khare
(74) *Attorney, Agent, or Firm*—Richard C. Litman

(57) ABSTRACT

A nutritional composition for the treatment of connective tissue in mammals which includes a glucosamine salt, chondroitin sulfate, collagen and sodium hyaluronate which synergistically act as a chondroprotective agent. The composition can further include a detoxifying agent, an anti-inflammatory agent or an analgesic to demonstrate additional therapeutic and physiologic properties. The nutritional composition acts as a chondro-protective agent which provides foundational support for the creation of new body tissue and cartilage growth in humans and animals.

19 Claims, No Drawings

NUTRITIONAL COMPOSITION FOR THE TREATMENT OF CONNECTIVE TISSUE

CROSS-REFERENCE TO RELATED APPLICATIONS

This application is a continuation-in-part of application Ser. No. 09/360,169 filed Jul. 26, 1999, now U.S. Pat. No. 6,476,005, which is a continuation-in-part of application Ser. No. 09/046,710 filed Mar. 24, 1998, and now abandoned.

BACKGROUND OF THE INVENTION

1. Field of the Invention

The present invention relates to therapeutic compositions which provide for the treatment of connective tissue in mammals and, more particularly to nutritional compositions capable of acting as chondroprotective agents, as well as exhibiting added pharmacological properties.

2. Description of the Related Art

The related art of interest discloses numerous pharmaceutical compositions and methods for the treatment of connective tissue in humans and animals. For example, U.S. Pat. No. 4,837,024 issued on Jun. 6, 1989, to Dov Michaeli describes topical compositions for improving wound healing comprising a suspension of particles of collagen and a glycosaminoglycan. The composition is taught to be useful for treating surface wounds by applying the composition to a gauze, bandage or the like.

U.S. Pat. No. 4,216,204 issued on Aug. 5, 1980, and U.S. Pat. No. 4,455,302 issued on Jun. 19, 1984, to Harry J. Robertson both disclose a medical protein hydrolysate containing an acetic acid extract of polypeptides and amino acids in the form of powder or a gel and produced from poultry feet. An aqueous solution can also be injected into a wound area such as burned animal regions. The composition is described as being useful for regrowing muscle, skin and nerve tissue.

U.S. Pat. No. 5,141,928 issued on Aug. 25, 1992, to Lawrence Goldman describes ophthalmic medications containing glycosaminoglycan polysulfates (GAGPS) or mucopolysaccharides having a molecular weight in the range of 5,000 to 20,000 Daltons combined with antibiotics for treating eye infections and antimicrobial agents such as pilocarpine or epinephrine for glaucoma. GAGPS include chondroitin sulfate and hyaluronic acid that contain hexosamines.

U.S. Pat. No. 5,840,715 issued on Nov. 24, 1998 to Vito Florio teaches a dietary regimen of nutritional supplements for relief of symptoms of arthritis. The dietary regimen comprises gamma linolenic acid (GLA), a mixture of eicosapentaenoic acid and docosahexaneoic acid (EPA) and a mixture of chondroitin sulfate, glucosamine sulfate and manganese asparate.

U.S. Pat. No. 5,442,053 issued on Aug. 15, 1995, to Francesco della Valle et al. describes a pharmaceutical composition and method for treating ophthalmic and dermatological conditions, diseases of the oral and nasal cavities or diseases of the outer ear by administering a salt of hyaluronic acid (alkali, alkali metal, magnesium, aluminum or ammonium) combined with a pharmacologically active substance such as erythromycin. The hyaluronic acid fraction has an average molecular weight of 30,000 to 730,000. The topical medicament can be applied as solids or in solution.

U.K. Patent Application No. 896,940 published on May 23, 1962, to Chas. Pfizer & Co. describes a healing agent for wounds of the body surface containing glucosamine and/or N-acetylglucosamine and glucosamine phosphate in a saline solution It has further been suggested by various prior art disclosures to use exclusively "nutraceuceuticals" or compositions containing only naturally-occurring components for treating connective tissue afflictions. For example, U.S. Pat. Nos. 5,364,845 issued on Nov. 15, 1994 and 5,587,363 issued Dec. 24, 1996, both to Robert W. Henderson describe therapeutic compositions administered in capsules form for the protection, treatment and repair of connective tissue in mammals. The compositions contain 250–3000 mg glucosamine hydrochloride or sulfate, 50–1000 mg chondroitin sulfate, and can additionally comprise 15–950 mg manganese ascorbate.

In other related art, Body Ammo Nutraceuticals in a "Product Alert" article, published Oct. 27, 1997, discloses capsules containing curcumin, hyaluronic acid, chondroitin sulfate and glucosamine. This product is stated to provide nutritional support for connective tissue. Further, Richardson Labs, Inc. in a "Lookout (Non Foods Edition)" abstract, published Sep. 9, 1997, discloses a product described as a food supplement containing hydrolyzed collagen, glucosamine and chondrotin sulfate that is described as being capable of reconstructing bone cartilage.

U.S. Pat. No. 5,929,050 issued on Jul. 27, 1999 to George D. Petito discloses a method and composition for treating open wounds by applying to the wound an effective amount of an aqueous solution of chrondroitin sulfate, which may optionally include collagen, sodium hyaluronate and/or glucosamine hydrochloride.

While all the above references have been describes as being effective for their intended use, there remains a need in the art for a therapeutic composition which demonstrates enhanced effectiveness in the treatment of connective tissues, exhibit other improved beneficial properties, and provide even wider applications in the modes of administration. The present invention meets these needs.

SUMMARY OF THE INVENTION

Accordingly, it is a principal object of the present invention to provide therapeutic compositions that are not only capable of effectively treating connective tissues in mammals, but demonstrate other beneficial physiological properties as well.

It is another object of the present invention to provide nutritional compositions for the treatment of connective tissues in humans and animals which can be formulated into various pharmaceutical dosage forms for oral, topical and parenteral administration.

It a further object of the present invention to provide nutritional compositions including chondroprotective agents which provides foundational support for the creation of new body tissue and cartilage growth in humans and animals.

Yet another object of the present invention is to provide nutritional compositions for promoting the healing of wounds in humans and animals, while reducing the associated pain and inflammation.

These and other objects are accomplished in accordance with the present invention by providing nutritional compositions comprising a therapeutically effective amount of a glucosamine salt, chondroitin sulfate, collagen and sodium hyaluronate which synergistically act as a chondroprotective agent. The nutritional compositions of the present invention are capable of being formulated into powder, capsule or tablet form for oral ingestion. The present compositions can also be prepared as a gel, paste or cream for topical application, or in a solution or suitable pharmaceutical carrier for oral or parenteral administration. Preferably, a detoxifying agent, an anti-inflammatory agent and/or an analgesic is incorporated into the formulations to provide added beneficial therapeutic and physiologic properties to the present compositions.

DETAILED DESCRIPTION OF THE PREFERRED EMBODIMENTS

The present invention provides an improvement over the compositions set forth in the aforementioned application Ser. No. 09/360,169 filed Jul. 26, 1999, the disclosure of which is incorporated herein by reference in its entirety. Thus, the present invention is directed to a nutritional composition comprising a therapeutically effective amount of a chondroprotective agent, preferably in combination with at least one other physiologically beneficial agent. The present nutritional composition comprises about 1–30 mg/kg of a glucosamine salt, about 1–15 mg/kg of chondroitin sulfate, about 1–30 mg/kg of collagen and about 1–15 mg/kg of sodium hyaluronate which synergistically act as the chondroprotective agent, wherein the dosage of each solid component present in the composition is expressed herein in terms of mg per kg bodyweight of the human to be treated. The unit dosages of the present compositions for animals may be substantially larger.

While the present compositions effectively provide foundational support for the creation of new body tissue and cartilage growth, facilitate chondrocyte synthesis, protect and maintain healthy muscle and tissue, increase hyaluronic acid concentrations, and reduce inflammation, other beneficial physiological properties of the compositions can be significantly enhanced by the incorporation of additional chemical agents. Preferably, a detoxifying agent, an anti-inflammatory agent and/or an analgesic is added to the present nutritional compositions for these intended purposes.

The glucosamine salt component of the present compositions is preferably the hydrochloride salt, but other salts of glucosamine such as the sulfate, nitrate or iodide obtained from either synthetic, bovine or porcine sources are also suitable. The chondroitin sulfate component may include Type A (chondroitin-4-sulfate), Type B (chondroitin-5-sulfate), and/or Type C (chondroitin-6-sulfate), obtained through fermentation or extraction of bovine trachea, other bovine or porcine sources. A molecular weight range of 2,000–50,000 can be used, with a preferred range of 25,000–35,000. The sodium hyaluronate component of the present compositions are obtained from either synthetic, bovine or avian sources with a molecular weight range from about 50,000 to about 3,500,000 Daltons. Both the chrondroitin sulfate and sodium hyaluronate components are glycosaminoglycans, commonly known as mucopolysaccharides.

All types of collagen, including native as well as hydrolyzed collagen, obtained from synthetic, avian, bovine or porcine sources would be suitable as the collagen component of the present compositions. The hydrolyzed collagen component can include hydrolyzed Type 1 collagen, preferably natural hydrolyzed collagen powder having a pH of 5.5–6.5, an ash content of 2.5% maximum, an isotonic point of 5.0–6.5. The hydrolyzed Type 1 collagen can have a molecular weight average up to 10,000 Daltons.

Other chemical agents which enhance the chondroprotective properties of the present nutritional compositions include a manganese salt and L-malic acid. A preferred salt is manganese ascorbate because it provides ascorbic acid for collagen synthesis, but other manganese salts such as the sulfate, nitrate, and gluconate can be used. The L-malic acid acts as a detoxifying agent by ridding the body of unwanted lactic acid, often found in connective tissue. Both the L-malic acid and manganese salt are preferably of U.S.P. food grade, and are present in the nutritional compositions of the present invention in dosages ranging from about 0.05 to about 8 mg/kg.

Pharmacological agents may be incorporated into the nutritional compositions of the present invention to significantly enhance the physiological properties of the compositions. The anti-inflammatory agents methy sulfonyl methane (MSM) and cetyl myristoleate may be added to reduce an inflammatory response. The MSM may be added in amounts of about 0.5–40 mg/kg, and cetyl myristoleate in amounts of 1–105 mg/kg. The present compositions may also be combined with aspirin, preferably in the range of about 0.1–35 mg/kg, and other commercially available analgesics to reduce pain. In addition, the incorporation of such vitamins as Vitamin C (ascorbic acid) and Vitamin $B_{12}$ in the present compositions provides added benefits to soft and hard tissues.

The nutritional compositions of the present invention are formulated into powder, capsule or tablet form for oral ingestion, Also, the present compositions are capable of being combined with a suitable pharmaceutical carrier and prepared as a gel, paste or cream for topical application. Alternatively, the compositions can be formulated in a solution or suitable pharmaceutical diluent for oral as well as parenteral administration.

For parenteral administration, the present compositions are preferably dissolved in sterilized water and buffered with such buffering agents as citric acid or sodium chloride to improve shelf life. The pH of the present solutions can be adjusted with conventional agents. Also, preservatives such as ethylene-diaminetetraacetic acid (EDTA), benzyl alcohol, and benzalkonium chloride can be added.

The nutritional compositions of the present invention provide an enhanced chondroprotective effect by providing foundational support for the creation of new body tissue and cartilage growth in mammals. The collagen component acts as a transporter or carrier for the larger molecules of sodium hyaluronate and/or chondroitin sulfate by aiding in the absorption process of these large molecules, thereby increasing the bio-availability of these therapeutic effective components.

It is to be understood that the present invention is not limited to the embodiments described above, but encompasses any and all embodiments within the scope of the following claims.

We claim:

1. A nutritional composition for the treatment of connective tissue in mammals comprising: a therapeutically effective amount of a glucosamine salt, chondroitin sulfate, collagen and sodium hyaluronate.

2. The nutritional composition according to claim 1, wherein the glucosamine salt is selected from the group consisting of glucosamine hydrochloride, glucosamine sulfate, glucosamine nitrate and glucosamine iodide.

3. The nutritional composition according to claim 1, wherein the collagen is hydrolyzed collagen.

4. The nutritional composition according to claim 3, wherein the hydrolyzed collagen is hydrolyzed Type 1 collagen having a molecular weight average up to 10,000 Daltons.

5. The nutritional composition according to claim 1, further comprising a manganese salt.

6. The nutritional composition according to claim 5, wherein the manganese salt is manganese ascorbate.

7. The nutritional composition according to claim 1, further comprising a detoxifying agent.

8. The nutritional composition according to claim 7, wherein the detoxifying agent is L-malic acid.

9. The nutritional composition according to claim 1, further comprising an anti-inflammatory agent.

10. The nutritional composition according to claim 9, wherein the an anti-inflammatory agent is selected from the group consisting of methy sulfonyl methane and cetyl myristoleate.

11. The nutritional composition according to claim 1, further comprising an analgesic.

12. The nutritional composition according to claim 11, wherein the analgesic is aspirin.

13. The nutritional composition according to claim 1, further comprising a vitamin selected from the group consisting of Vitamin C and Vitamin $B_{12}$.

14. The nutritional composition according to claim 1, wherein the composition is formulated into a unit dosage form for oral administration.

15. The nutritional composition according to claim 1, wherein the composition is combined with a suitable pharmaceutical carrier and prepared as a gel, paste or cream for topical application.

16. The nutritional composition according to claim 1, wherein the composition is formulated in a solution or suitable pharmaceutical diluent for oral or parenteral administration.

17. The nutritional composition according to claim 1, wherein the composition comprises, based on mg/kg of bodyweight:

about 1–30 mg/kg of a glucosamine salt;

about 1–15 mg/kg of chondroitin sulfate;

about 1–30 mg/kg of collagen; and about 1–15 mg/kg of sodium hyaluronate.

18. The nutritional composition according to claim 17, further including a manganese salt ranging from about 0.05 to about 8 mg/kg.

19. The nutritional composition according to claim 17, further including L-malic acid ranging from about 0.05 to about 8 mg/kg.

* * * * *